US012753162B2

(12) United States Patent
Kobayashi et al.

(10) Patent No.: US 12,753,162 B2
(45) Date of Patent: Oct. 6, 2026

(54) METHOD FOR PRODUCING 2-HETEROARYLPYRIDINE COMPOUND

(71) Applicant: Nippon Soda Co., Ltd., Tokyo (JP)

(72) Inventors: Shinichi Kobayashi, Takaoka (JP); Hirokazu Matsuda, Takaoka (JP)

(73) Assignee: NIPPON SODA CO., LTD., Tokyo (JP)

( * ) Notice: Subject to any disclaimer, the term of this patent is extended or adjusted under 35 U.S.C. 154(b) by 239 days.

(21) Appl. No.: 18/696,186

(22) PCT Filed: Nov. 16, 2022

(86) PCT No.: PCT/JP2022/042495

§ 371 (c)(1),
(2) Date: Mar. 27, 2024

(87) PCT Pub. No.: WO2023/090344

PCT Pub. Date: May 25, 2023

(65) Prior Publication Data

US 2024/0391894 A1 Nov. 28, 2024

(30) Foreign Application Priority Data

Nov. 19, 2021 (JP) ................................ 2021-188982

(51) Int. Cl.
*C07D 401/04* (2006.01)

(52) U.S. Cl.
CPC ................................ *C07D 401/04* (2013.01)

(58) Field of Classification Search
CPC ............................ C07D 401/04; C07D 233/64
(Continued)

(56) References Cited

U.S. PATENT DOCUMENTS 4,410,706 A 10/1983 Rothenberg et al.
4,886,891 A 12/1989 Torii et al.
(Continued)

FOREIGN PATENT DOCUMENTS

CA 3115968 A1 5/2020
CN 101100454 A 1/2008
(Continued)

OTHER PUBLICATIONS

Database Registry [Online] Chemical Abstract Service, Columbus, Ohio, US; Nov. 9, 2011 (Nov. 9, 2011), XP093315452, Database accession No. 1343121-58-3, 1341679-36-4, 1339522-22-3 (cited in a Search dated Oct. 14, 2025 in EP App. No. 22895618.1).
Yoshida Y et al: "TiCl'4/Bu'3N/(catalytic TMSOTf): Efficient Agent for Direct Aldol Addition and Claisen Condensation", Tetrahedron Letters, Elsevier, Amsterdam, NL, vol. 38, No. 50, Dec. 15, 1997 (Dec. 15, 1997), pp. 8727-8730, XP004097162, ISSN: 0040-4039, DOI: 10.1016/S0040-4039(97)10320-3 (cited in a Search dated Oct. 16, 2025 in EP App. 22895626.4).
Search report dated Oct. 14, 2025 in EP App. No. 22895618.1.
Search report dated Oct. 16, 2025 in EP App. No. 22895626.4.
Wikipedia: "Wikipedia", "Sodium dithionite", Jan. 1, 1997 (Jan. 1, 1997), XP093314749, Retrieved from the Internet: URL:https://en.wikipedia.org/wiki/Sodium_dithionite.
(Continued)

*Primary Examiner* — James H Alstrum-Acevedo
*Assistant Examiner* — Sahar Inam
(74) *Attorney, Agent, or Firm* — FITCH, EVEN, TABIN & FLANNERY, LLP

(57) ABSTRACT

The present invention provides a method for producing a compound represented by formula (3) (in the formula, Q, $R^1$ and $R^2$ are the same as those in formula (1) and formula (2)), comprising chemically reacting a compound represented by formula (1) (in the formula, Q represents a substituted or unsubstituted 5- to 6-membered or 9- to 10-membered heteroaryl group, and $R^1$ represents a C1-6 alkyl group) with a compound represented by formula (2) (in the formula, $R^2$ represents a hydrogen atom, a substituted or unsubstituted C1-6 alkyl group, a substituted or unsubstituted C3-6 cycloalkyl group, a substituted or unsubstituted phenyl group, or a substituted or unsubstituted 5- to 6-membered heteroaryl group) in the presence of a metal alkoxide or a base, and a method for producing a compound represented by formula (4) (in the formula, Q, $R^1$ and $R^2$ are the same as those in formula (3)), comprising chemically reacting the compound represented by formula (3) with a hydroxylamine or a salt thereof, and subjecting a product of the chemical reaction to a dehydration reaction, (1)

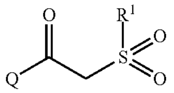

(2)

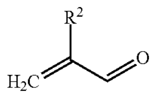

(3)

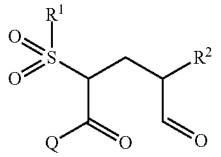

(4)

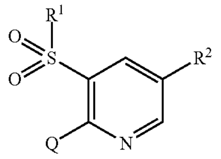

2 Claims, No Drawings

(58) Field of Classification Search
USPC .......................................................... 514/256
See application file for complete search history.

(56) References Cited

U.S. PATENT DOCUMENTS

| | | | |
|---|---|---|---|
| 2018/0362470 A1 | 12/2018 | Hamamoto et al. | |
| 2019/0185459 A1 | 6/2019 | Sakanishi et al. | |
| 2020/0010445 A1 | 1/2020 | Kimura et al. | |
| 2021/0269415 A1 | 9/2021 | Sakanishi et al. | |
| 2021/0380554 A1 | 12/2021 | Sakanishi et al. | |
| 2021/0380556 A1 | 12/2021 | Sakanishi et al. | |
| 2022/0002342 A1* | 1/2022 | Macmillan | C07K 1/113 |

FOREIGN PATENT DOCUMENTS

| | | | | |
|---|---|---|---|---|
| CN | 103420783 A | | 12/2013 | |
| CN | 106866515 A | | 6/2017 | |
| EP | 0 187 674 A2 | | 7/1986 | |
| EP | 3252046 A1 | | 12/2017 | |
| EP | 3372588 A1 | * | 9/2018 | A61P 33/10 |
| JP | 58-210067 A | | 12/1983 | |
| JP | 61-161225 A | | 7/1986 | |
| JP | 63-264429 A | | 11/1988 | |
| JP | 04-021672 A | | 1/1992 | |
| JP | 2000-178247 A | | 6/2000 | |
| JP | 2011-121913 A | | 6/2011 | |
| JP | 2017-066077 A | | 4/2017 | |
| JP | 2019-019068 A | | 2/2019 | |
| JP | 2019065018 | * | 3/2019 | |
| JP | 2019-065018 A | | 4/2019 | |
| JP | 2022-038431 A | | 3/2022 | |
| TW | 201726628 A | | 8/2017 | |
| TW | 202024054 A | | 7/2020 | |
| WO | WO-2005/090333 A1 | | 9/2005 | |
| WO | 2009/054742 A2 | | 4/2009 | |
| WO | WO-2017/016910 A1 | | 2/2017 | |
| WO | WO-2017/050685 A1 | | 3/2017 | |
| WO | WO-2017/104741 A1 | | 6/2017 | |
| WO | 2018/052035 A1 | | 3/2018 | |
| WO | WO-2018/194077 A1 | | 10/2018 | |
| WO | WO-2020/050212 A1 | | 3/2020 | |
| WO | WO-2020/071304 A1 | | 4/2020 | |
| WO | WO-2020090585 A1 | * | 5/2020 | C07D 401/04 |
| WO | WO-2023090344 A1 | * | 5/2023 | C07D 401/04 |

OTHER PUBLICATIONS

Search Report dated Oct. 15, 2025 in EP App. No. 22895617.3.
Office Action dated Jan. 19, 2026 in TW App. No. 111143657 with translation of search report.
Office Action dated Jan. 21, 2026 in TW App. No. 111143659 with translation of search report.
Huang H, Cai J, Tang L, Wang Z, Li F, Deng GJ. "Metal-Free Assembly of Polysubstituted Pyridines from Oximes and Acroleins", J Org Chem. Feb. 19, 2016; 81(4): 1499-505. doi: 10.1021/acs.joc.5b02624. Epub Jan. 28, 2016. PMID: 26788938. Jan. 28, 2016 (cited in an Office Action dated Jan. 15, 2026 in India App. No. 202447022078).
Ye Wei, Naohiko Yoshikai; "Modular Pyridine Synthesis from Oximes and Enals through Synergistic Copper/Iminium Catalysis"; J. Am. Chem. Soc. 2013, 135, 10, 3756-3759; https://doi.org/10.1021/ja312346s; Feb. 26, 2013 (Feb. 26, 2013) (cited in an Office Action dated Jan. 15, 2026 in India App. No. 202447022078).
Office Action dated Jan. 15, 2026 in IN App. No. 202447022078.
International Search Report dated Feb. 7, 2023 in PCT/JP2022/042473.
International Search Report dated Jan. 24, 2023 in PCT/JP2022/042474.
International Search Report dated Jan. 24, 2023 in PCT/JP2022/042495.
International Search Report dated Jan. 31, 2023 in PCT/JP2022/042500.
Marcoux et al., "A General Preparation of Pyridines and Pyridones via the Annulation of Ketones and Esters," J. Org. Chem., 2001, 66:4194-4199.
Takagi et al., "Synthesis of Fluorine Compounds Using Zing Complex of Halothane," Tetrahedron, 1996, 52(39):12667-12676.
Hilf, J. A., et al., Route to highly substituted pyridines, The Journal of Organic Chemistry, Aug. 31, 2016, vol. 81, No. 21, pp. 10376-10382 (cited in a Notice of Allowance dated Apr. 7, 2026 in JP App. No. 2023-562366).
Office Action dated Apr. 7, 2026 in JP App. No. 2023-562359.
Notice of Allowance dated Apr. 7, 2026 in JP App. No. 2023-562366.
Hashimoto et al., (2006), "Practical method for the synthesis of (R)-homopipecolinic acid and (R)-homoproline esters from w-chloroalkanoic acids and available chiral amines," Tetrahedron, 62, p. 2214-2223. (Year: 2006).
O'Brien et al., (2014), "Radical C-H Functionalization of Heteroarenes under Electrochemical Control," Angewandte Chemie International Edition, 53(44), p. 11868-11871. (Year: 2014).
Huang et al., (2019), "Electricity-driven asymmetric Lewis acid catalysis," Nature Catalysis, 2, p. 34-40 (Year: 2019).
Quayle Action dated Jun. 30, 2026 in U.S. Appl. No. 18/694,784.

* cited by examiner

METHOD FOR PRODUCING 2-HETEROARYLPYRIDINE COMPOUND

CROSS-REFERENCE TO RELATED APPLICATIONS

This application is the U.S. National Stage of PCT/JP2022/042495, filed Nov. 16, 2022, which claims priority to JP 2021-188982, filed Nov. 19, 2021.

TECHNICAL FIELD

The present invention relates to a method for producing a 2-heteroarylpyridine compound.

BACKGROUND ART

Nitrogen-containing heterocycles are a major partial structure (building blocks) constituting compounds that serve as active ingredients for pharmaceuticals and agricultural chemicals. In recent years, arthropod pest control agents having a pyridine ring have been actively developed. For example, Patent Documents 1 to 5 describe pyridine compounds having a 5-membered heteroaryl group and a sulfur-containing hydrocarbon group.

In addition, Non-Patent Document 1 discloses that a 3-phenyl-5-chloro-2-pyridone (4 g) and a 3-hydroxycarbonyl-5-chloro-2-pyridone (4 h) were produced by reacting a 2-chloro-N,N-dimethylamino trimethinium hexafluorophosphate with a methylphenylacetate and a 3-methoxy-3-oxopropanoic acid.

[Chemical formula 1]

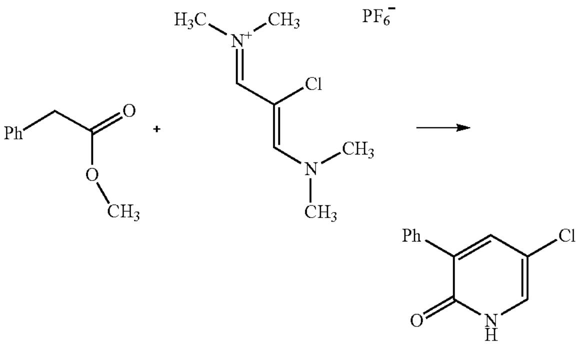

4g

[Chemical formula 2]

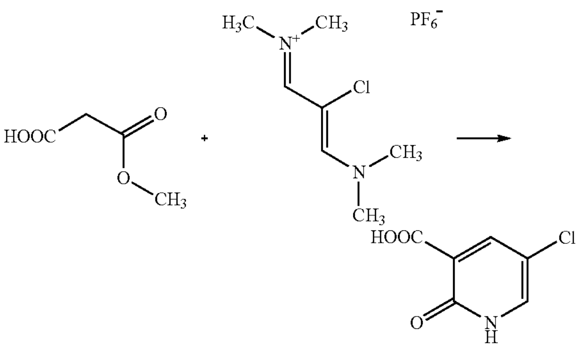

4h

Patent Document 6 discloses a method for constructing a pyridine ring according to the following scheme.

[Chemical formula 3]

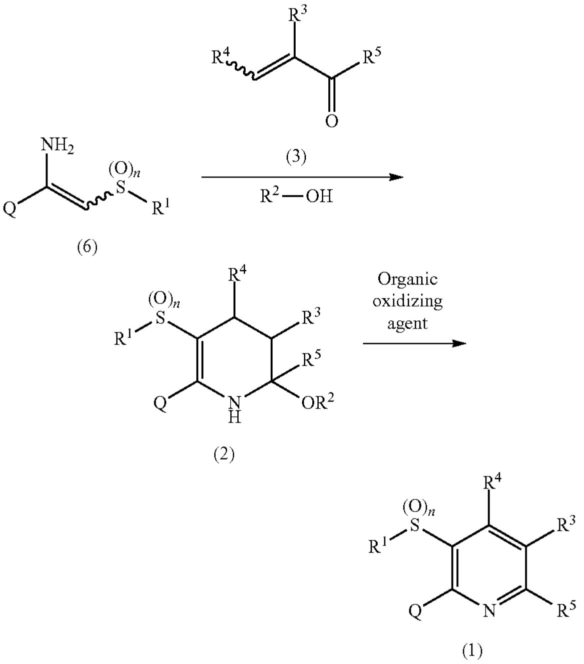

(6)

(2)

(1)

In the above scheme, Q represents a pyridyl group or the like, $R^1$ represents a C1-C6 alkyl group which may have one or more halogen atoms, $R^2$ represents a C1-C6 alkyl group or the like which may have one or more halogen atoms, $R^3$, $R^4$ and $R^5$ each represent a hydrogen atom, and n represents 0 or the like.

CITATION LIST

Patent Literature

[Patent Document 1] WO 2017/016910 A
[Patent Document 2] WO 2017/050685 A
[Patent Document 3] WO 2020/050212 A
[Patent Document 4] WO 2020/071304 A
[Patent Document 5] WO 2020/090585 A
[Patent Document 6] WO 2018/194077 A

Non-Patent Literature

[Non-Patent Document 1] Jean-Francuois Marcoux et al. "A General Preparation of Pyridines and Pyridones via the Annulation of Ketones and Esters" J. Org. Chem., Vol. 66, No. 12, 2001, 4194-4199.

SUMMARY OF INVENTION

Technical Problem

An object of the present invention is to provide a method for producing a 2-heteroarylpyridine compound having a sulfur-containing functional group, which is one of the building blocks.

Solution to Problem

As a result of repeated studies to achieve the above object, the present invention including the following aspects has been completed.

[1] A method for producing a compound represented by formula (3) (hereinafter sometimes referred to as compound (3)), comprising:

chemically reacting a compound represented by formula (1) (hereinafter sometimes referred to as compound (1)) with a compound represented by formula (2) (hereinafter sometimes referred to as compound (2)) in the presence of a metal alkoxide or a base.

[Chemical formula 4]

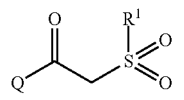

(1)

(In formula (1), Q represents a substituted or unsubstituted 5- to 6-membered or 9- to 10-membered heteroaryl group, and $R^1$ represents a C1-6 alkyl group.)

[Chemical formula 5]

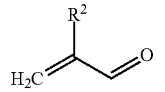

(2)

(In formula (2), $R^2$ represents a hydrogen atom, a substituted or unsubstituted C1-6 alkyl group, a substituted or unsubstituted C3-6 cycloalkyl group, a substituted or unsubstituted phenyl group, or a substituted or unsubstituted 5- to 6-membered heteroaryl group.)

[Chemical formula 6]

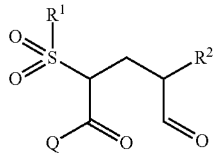

(3)

(In formula (3), Q, $R^1$ and $R^2$ are the same as those in formula (1) and formula (2).)

[2] The method according to [1], wherein Q in formula (1) and formula (3) is a group represented by formula (5).

[Chemical formula 7]

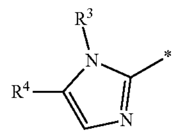

(5)

(In formula (5), * represents a bonding site, $R^3$ represents a C1-6 alkyl group, $R^4$ represents a hydrogen atom, a substituted or unsubstituted C1-6 alkyl group, a substituted or unsubstituted C2-6 alkenyl group, or a 1,3-dioxolan-2-yl group.)

[3] A method for producing a compound represented by formula (4) (hereinafter sometimes referred to as compound (4)), comprising:

chemically reacting a compound represented by formula (3) (hereinafter sometimes referred to as compound (3)) with a hydroxylamine or a salt thereof, and subjecting a product of the above chemical reaction to a dehydration reaction.

[Chemical formula 8]

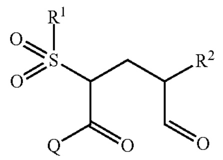

(3)

(In formula (3), Q represents a substituted or unsubstituted 5- to 6-membered or 9- to 10-membered heteroaryl group, $R^1$ represents a C1-6 alkyl group, and $R^2$ represents a hydrogen atom, a substituted or an unsubstituted C1-6 alkyl group, a substituted or unsubstituted C3-6 cycloalkyl group, a substituted or unsubstituted phenyl group, or a substituted or unsubstituted 5- to 6-membered heteroaryl group.)

[Chemical formula 9]

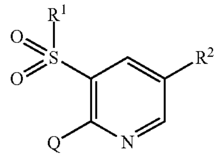

(4)

(In formula (4), Q, $R^1$ and $R^2$ are the same as those in formula (3).)

[4] A method for producing a compound represented by formula (4), comprising:

chemically reacting a compound represented by formula (3) with an ammonia or an ammonium salt in the presence of an alcohol, and oxidizing a product of the above chemical reaction in the presence of an organic oxidizing agent.

[Chemical formula 8]

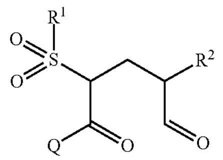

(3)

(In formula (3), Q represents a substituted or unsubstituted 5- to 6-membered or 9- to 10-membered heteroaryl group, $R^1$ represents a C1-6 alkyl group, and $R^2$ represents a hydrogen atom, a substituted or an unsubstituted C1-6 alkyl group, a substituted or unsubstituted C3-6 cycloalkyl group, a substituted or unsubstituted phenyl group, or a substituted or unsubstituted 5- to 6-membered heteroaryl group.)

[Chemical formula 11]

(4)

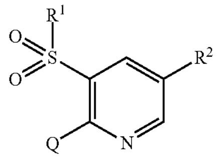

(In formula (4), Q, $R^1$ and $R^2$ are the same as those in formula (3).)

[5] The method according to [3] or [4], wherein Q in formula (3) and formula (4) is a group represented by formula (5).

[Chemical formula 12]

(5)

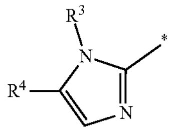

(In formula (5), * represents a bonding site, $R^3$ represents a C1-6 alkyl group, $R^4$ represents a hydrogen atom, a substituted or unsubstituted C1-6 alkyl group, a substituted or unsubstituted C2-6 alkenyl group, or a 1,3-dioxolan-2-yl group.)

[6] A compound represented by formula (3a).

[Chemical formula 13]

(3a)

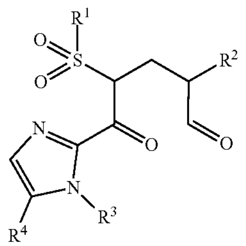

(In formula (3a), $R^1$ represents a C1-6 alkyl group, $R^2$ represents a hydrogen atom, a substituted or unsubstituted C1-6 alkyl group, a substituted or unsubstituted C3-6 cycloalkyl group, a substituted or unsubstituted phenyl group, or a substituted or unsubstituted 5- to 6-membered heteroaryl group, $R^3$ represents a C1-6 alkyl group, and $R^4$ represents a hydrogen atom, a substituted or unsubstituted C1-6 alkyl group, a substituted or unsubstituted C2-6 alkenyl group, or a 1,3-dioxolan-2-yl group.)

Advantageous Effects of Invention

According to the production method of the present invention, a compound represented by formula (3) and a compound represented by formula (4) can be obtained in high yield.

DESCRIPTION OF EMBODIMENTS

In the present invention, the term "unsubstituted" refers to a group having only a mother nucleus. When "substituted" is not mentioned and only the name of the mother nucleus is described, it means "unsubstituted" unless otherwise specified.

On the other hand, the term "substituted" means that any hydrogen atom of the group serving as a mother nucleus is substituted with a group (substituent) having the same or different structure from the mother nucleus. Therefore, a "substituent" is another group bonded to the mother nucleus. The number of substituents may be one, or two, or more. Two or more substituents may be the same or different.

A term such as "C1-6" indicates that the number of carbon atoms in the group serving as a mother nucleus is 1 to 6. This number of carbon atoms does not include the number of carbon atoms present in the substituents. For example, a butyl group having an ethoxy group as a substituent is classified as a C2 alkoxy C4 alkyl group.

The "substituent" is not particularly limited as long as it is chemically permissible and has the effects of the present invention.

Examples of the groups that can be the "substituent" are shown below.

C1-6 alkyl groups such as a methyl group, an ethyl group, an n-propyl group, an i-propyl group, an n-butyl group, an s-butyl group, an i-butyl group, a t-butyl group, an n-pentyl group, an n-hexyl group or the like;

C2-6 alkenyl groups such as a vinyl group, a 1-propenyl group, a 2-propenyl group (allyl group), a 1-butenyl group, a 2-butenyl group, a 3-butenyl group, a 1-methyl-2-propenyl group, a 2-methyl-2-propenyl group or the like;

C2-6 alkynyl groups such as an ethynyl group, a 1-propynyl group, a 2-propynyl group, a 1-butynyl group, a 2-butynyl group, a 3-butynyl group, a 1-methyl-2-propynyl group or the like;

C3-6 cycloalkyl groups such as a cyclopropyl group, a cyclobutyl group, cyclopentyl group, a cyclohexyl group or the like;

a phenyl group;

3- to 6-membered heterocyclyl groups;

C1-6 alkoxy groups such as a methoxy group, an ethoxy group, an n-propoxy group, an i-propoxy group, an n-butoxy group, an s-butoxy group, an i-butoxy group, a t-butoxy group or the like;

C6-10 aryloxy groups such as a phenoxy group, a naphthoxy group or the like;

5- to 6-membered heteroaryloxy groups such as a thiazolyloxy group, a pyridyloxy group or the like;

C1-6 alkoxycarbonyl groups such as a methoxycarbonyl group, an ethoxycarbonyl group, an n-propoxycarbonyl group, an i-propoxycarbonyl group, an n-butoxycarbonyl group, a t-butoxycarbonyl group or the like;

halogeno groups such as a fluoro group, a chloro group, a bromo group, an iodo group or the like;

C1-6 haloalkyl groups such as a chloromethyl group, a chloroethyl group, a trifluoromethyl group, a 1,2-dichloro-n-propyl group, a 1-fluoro-n-butyl group, a perfluoro-n-pentyl group or the like;

C1-6 haloalkoxy groups such as a trifluoromethoxy group, a 2-chloro-n-propoxy group, a 2,3-dichlorobutoxy group or the like;

a formylamino group;

C1-6 alkylcarbonylamino groups such as an acetylamino group, a propanoylamino group, a butyrylamino group, an i-propylcarbonylamino group or the like;

C1-6 alkoxycarbonylamino groups such as a methoxycarbonylamino group, an ethoxycarbonylamino group, an n-propoxycarbonylamino group, an i-propoxycarbonylamino group or the like;

Unsubstituted or substituted aminocarbonyl groups such as an aminocarbonyl group, a dimethylaminocarbonyl group, a phenylaminocarbonyl group, an N-phenyl-N-methylaminocarbonyl group or the like;

C1-6 alkylthio groups such as a methylthio group, an ethylthio group, an n-propylthio group, an i-propylthio group, an n-butylthio group, an i-butylthio group, an s-butylthio group, a t-butylthio group or the like;

C1-6 haloalkylthio groups such as a trifluoromethylthio group, a 2,2,2-trifluoroethylthio group or the like;

C1-6 alkylsulfonyl groups such as a methylsulfonyl group, an ethylsulfonyl group, a t-butylsulfonyl group or the like;

C1-6 haloalkylsulfonyl groups such as a trifluoromethylsulfonyl group, a 2,2,2-trifluoroethylsulfonyl group or the like;

a cyano group; a nitro group;

Moreover, any hydrogen atom in these "substituents" may be substituted with a group having a different structure. Examples of the substituent in this case include a C1-6 alkyl group, a C1-6 haloalkyl group, a C1-6 alkoxy group, a C1-6 haloalkoxy group, a halogeno group, a cyano group and a nitro group.

Furthermore, the above-mentioned "3- to 6-membered heterocyclyl group" includes 1 to 4 heteroatoms selected from the group consisting of a nitrogen atom, an oxygen atom and a sulfur atom as a ring constituent atom. The heterocyclyl group may be monocyclic or polycyclic. In the polycyclic heterocyclyl group, as long as at least one ring is a heterocyclic ring, the remaining rings may be any of a saturated alicyclic ring, an unsaturated alicyclic ring or an aromatic ring. Examples of the "3- to 6-membered heterocyclyl group" include a 3- to 6-membered saturated heterocyclyl group, a 5- to 6-membered heteroaryl group, a 5- to 6-membered partially unsaturated heterocyclyl group and the like.

Examples of the 3- to 6-membered saturated heterocyclyl group include an aziridinyl group, an epoxy group, a pyrrolidinyl group, a tetrahydrofuranyl group, a thiazolidinyl group, a piperidyl group, a piperazinyl group, a morpholinyl group, a dioxolanyl group, a dioxanyl group and the like.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, a tetrazolyl group and the like.

Examples of the 6-membered heteroaryl group include a pyridyl group, a pyrazinyl group, a pyrimidinyl group, a pyridazinyl group, and a triazinyl group.

Examples of the 5-membered partially unsaturated heterocyclyl group include a pyrrolinyl group, a dihydrofuranyl group, an imidazolinyl group, a pyrazolinyl group, an oxazolinyl group, an isoxazolinyl group and the like.

Examples of the 6-membered partially unsaturated heterocyclyl group include a dihydropyranyl group and the like.

<Method for Producing Compound (3)>

The method for producing compound (3) according to the present invention includes chemically reacting compound (1) with compound (2) in the presence of a metal alkoxide or a base (hereinafter sometimes referred to as the first reaction).

Compound (1)

Compound (1) is represented by formula (1).

[Chemical formula 14]

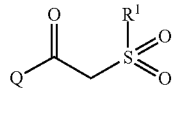

(1)

In formula (1), $R^1$ represents a C1-6 alkyl group.

The C1-6 alkyl group for $R^1$ may be linear or branched. Examples of the C1-6 alkyl group for $R^1$ include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group, an i-hexyl group and the like.

In formula (1), Q represents a substituted or unsubstituted 5- to 6-membered or 9- to 10-membered heteroaryl group.

Examples of the "5-membered heteroaryl group" include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, a tetrazolyl group and the like.

Examples of the "6-membered heteroaryl group" include a pyridyl group, a pyrazinyl group, a pyrimidinyl group, a pyridazinyl group, a triazinyl group and the like.

Examples of the "9-membered heteroaryl group" include an indolyl group, an isoindolyl group, a benzofuranyl group, a benzothienyl group, an indazolyl group, a benzimidazolyl group, a benzoxazolyl group, a benzisoxazolyl group, a benzothiazolyl group, a benzisothiazolyl group and the like.

Examples of the "10-membered heteroaryl group" include an isoquinolinyl group, a quinazolinyl group, a 1,2,4-benzotriazinyl group, a 1,2,3,4-benzotetrazinyl group, and the like.

Substituents on the "5- to 6-membered or 9- to 10-membered heteroaryl group" for Q include halogeno groups such as a fluoro group, a chloro group, a bromo group, an iodo group or the like; C1-6 alkyl groups such as a methyl group, an ethyl group, an n-propyl group, an i-propyl group, an n-butyl group, an s-butyl group, an i-butyl group, a t-butyl group, an n-pentyl group, an n-hexyl group or the like; C1-6 haloalkyl groups such as a difluoromethyl group, a trifluoromethyl group, a perfluoroethyl group, a 1,2,2,3,3,3-hexafluoropropyl group, a perfluoropropyl group, a 1,2,3,3,3-pentafluoro-2-(trifluoromethyl) propyl group or the like; C2-6 alkynyl groups such as an ethynyl group, a 1-propynyl group, a 2-propynyl group, a 1-butynyl group, a 2-butynyl group, a 3-butynyl group, a 1-methyl-2-propynyl group or the like; C2-6 haloalkynyl groups such as a 3,3,4,4,4-pentafluorobut-1-en-1-yl group, a 2-chloro-3,3,3-trifluoroprop-1-en-1-yl group, a 2,2-dichloroethenyl group, a 2,3,3,4,4,4-hexafluorobut-1-en-1-yl group, a 2-chloro- 3,3,4,4,4-pentafluorobut-1-en-1-yl group or the like; C1-6 alkoxy groups such as a methoxy group, an ethoxy group, an n-propoxy group, an i-propoxy group, an n-butoxy group, an s-butoxy group, an i-butoxy group, a t-butoxy group or the like; C1-6 haloalkoxy groups such as a difluoromethoxy group, a trifluoromethoxy group, a 2,2-difluoroethyl group, a 2,2,2-trifluoroethyl group or the like; a phenyl group; phenyl groups substituted with a halogeno group, a C1-6 alkyl group, a C1-6 haloalkyl group or a C1-6 haloalkoxy group, such as a 4-chlorophenyl, a 4-methylphenyl group, a 4-trifluoromethylphenyl group, a 4-trifluoromethoxyphenyl group or the like; a formyl group, a dimethoxymethyl group, a diethoxymethyl group, a 1,3-dioxolan-2-yl group or a cyano group; and the like.

In the present invention, Q is preferably a group represented by formula (5).

[Chemical formula 15]

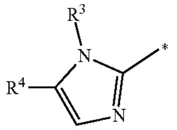

(5)

In formula (5), * represents a bonding site, $R^3$ represents a C1-6 alkyl group, $R^4$ represents a hydrogen atom, a substituted or unsubstituted C1-6 alkyl group, a substituted or unsubstituted C2-6 alkenyl group or a 1,3-dioxolan-2-yl group.

Specifically, compound (1) is preferably a compound represented by formula (1a) (hereinafter sometimes referred to as compound (1a)).

[Chemical formula 16]

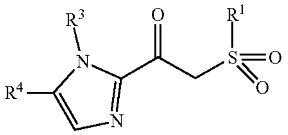

(1a)

In formula (1a), $R^1$ represents a C1-6 alkyl group, $R^3$ represents a C1-6 alkyl group, $R^4$ represents a hydrogen atom, a substituted or unsubstituted C1-6 alkyl group, a substituted or unsubstituted C2-6 alkenyl group or a 1,3-dioxolan-2-yl group.

Compound (1a) is particularly useful as a substrate in the production method of the present invention.

The C1-6 alkyl group for $R^3$ and $R^4$ can be the same as that for $R^1$.

Examples of the C2-6 alkenyl group for $R^4$ include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group and the like.

Substituents on the "C1-6 alkyl group" and the "C2-6 alkenyl group" for $R^4$ include halogeno groups such as a fluoro group, a chloro group, a bromo group, an iodo group or the like; a hydroxyl group; C1-6 alkoxy groups such as a methoxy group, an ethoxy group, an n-propoxy group, an i-propoxy group, an n-butoxy group, an s-butoxy group, an i-butoxy group, a t-butoxy group or the like; C1-6 haloalkoxy groups such as a 2-chloro-n-propoxy group, a 2,3-dichloro butoxy group, a trifluoromethoxy group or the like; a phenyl group; phenyl groups substituted with a halogeno group, a C1-6 haloalkyl group or a C1-6 haloalkyl group, such as a 4-chlorophenyl group, a 4-trifluoromethylphenyl group, a 4-trifluoromethoxyphenyl group or the like; and a cyano group. Among these, halogeno groups are preferred.

Examples of the halogeno-substituted C1-6 alkyl group for $R^4$ include a fluoromethyl group, a difluoromethyl group, a trifluoromethyl group, a 2,2,2-trifluoroethyl group, a pentafluoroethyl group, a 3,3,3-trifluoro propyl group, a 2,2,3,3,3-pentafluoropropyl group, a 1-chloro-2,2,3,3,3-pentafluoropropyl group, a 1,2,2,3,3,3-hexafluoropropyl group, a perfluoropropyl group, a 2,2,2-trifluoro-1-trifluoromethylethyl group, a perfluoroisopropyl group, a 4-fluorobutyl group, a 1,4,4,4-tetrafluorobutyl group, a 2,2,3,3,4,4,4-heptafluorobutyl group, a 1,2,2,3,3,4,4,4-octafluorobutyl group, a perfluorobutyl group, a 3,3,3-trifluoro-2-trifluoromethylpropyl group, a 1-chloro-2,3,3,3-tetrafluoro-2-trifluoromethylpropyl group, a 1,2,3,3,3-pentafluoro-2-trifluoromethylpropyl group, a perfluoropentyl group, a perfluorohexyl group and the like.

Examples of the halogeno-substituted C2-6 alkenyl group for $R^4$ include C2-6 haloalkenyl groups such as a 2,3,3,3-tetrafluoro-1-propenyl group, a 3,3,3-trifluoro-1-propenyl group, a 2-chloro-3,3,3-trifluoro-1-propenyl group, a 2-bromo-3,3,3-trifluoro-1-propenyl group, a 3,3,3-trifluoro-2-trifluoromethyl-1-propenyl group, a 3,3,4,4,4-pentafluoro-1-butenyl group, a 2,3,3,4,4,4-hexafluoro-1-butenyl group, a 2-chloro-3,3,4,4,4-pentafluoro-1-butenyl group or the like, and the like.

$R^4$ is preferably a 2-chloro-3,3,3-trifluoro-1-propenyl group. The stereoisomerism of the 2-chloro-3,3,3-trifluoro-1-propenyl group may be a mixture of E form/Z form, or may be a Z form alone or an E form alone.

Compound (1) used in the present invention may be one synthesized using a known method, or may be one synthesized by another method and commercially available. Specifically, the following compounds can be mentioned.

[Chemical formula 17]

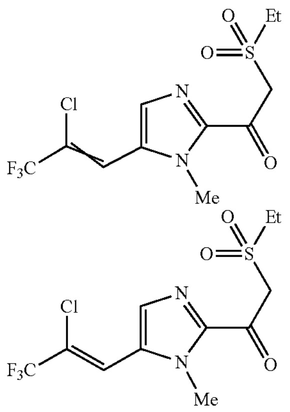

The following notation in the chemical formula is an undefined double stereo bond.

[Chemical formula 18]

Compound (2)

Compound (2) is represented by formula (2).

[Chemical formula 19]

(2)

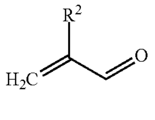

In formula (2), $R^2$ is a hydrogen atom, substituted or unsubstituted C1-6 alkyl group, a substituted or unsubstituted C3-6 cycloalkyl group, a substituted or unsubstituted phenyl group, or a substituted or unsubstituted 5- to 6-membered heteroaryl group.

The C1-6 alkyl group for $R^2$ can be the same as the C1-6 alkyl group for $R^1$.

Examples of the substituents on the "C1-6 alkyl group" for $R^2$ include halogeno groups such as a fluoro, a chloro, a bromo, an iodo group or the like; a hydroxyl group; C1-6 alkoxy groups such as a methoxy group, an ethoxy group, an n-propoxy group, an i-propoxy group, an n-butoxy group, an s-butoxy group, an i-butoxy group, a t-butoxy group or the like; C1-6 haloalkoxy groups such as a 2-chloro-n-propoxy group, a 2,3-dichlorobutoxy group, a trifluoromethoxy group or the like; a phenyl group; phenyl groups substituted with a halogeno group, a C1-6 haloalkyl group or a C1-6 haloalkoxy group, such as a 4-chlorophenyl group, a 4-trifluoromethylphenyl group, a 4-trifluoromethoxyphenyl group or the like; and a cyano group. Among these, a halogeno group is preferable.

Examples of the halogeno-substituted C1-6 alkyl group include a fluoromethyl group, a difluoromethyl group, a trifluoromethyl group, a 2,2,2-trifluoroethyl group, a pentafluoroethyl group, a 3,3,3-trifluoropropyl group, a 2,2,3,3,3-pentafluoropropyl group, a 1-chloro-2,2,3,3,3-pentafluoropropyl group, a 1,2,2,3,3,3-hexafluoropropyl group, a perfluoropropyl group, a 2,2,2-trifluoro-1-trifluoromethylethyl group, a perfluoroisopropyl group, a 4-fluorobutyl group, a 1,4,4,4-tetrafluorobutyl group, a 2,2,3,3,4,4,4-heptafluorobutyl group, a 1,2,2,3,3,4,4,4-octafluorobutyl group, a perfluorobutyl group, a 3,3,3-trifluoro-2-trifluoromethylpropyl group, a 1-chloro-2,3,3,3-tetrafluoro-2-trifluoromethylpropyl group, a 1,2,3,3,3-pentafluoro-2-trifluoromethylpropyl group, a perfluoropentyl group, a perfluorohexyl group and the like.

Examples of the C3-6 cycloalkyl group for $R^2$ include a cyclopropyl group, a cyclobutyl group, a cyclopentyl group, a cyclohexyl group and the like.

The 5- to 6-membered heteroaryl group for $R^2$ is a 5- or 6-membered ring containing 1, 2, 3, or 4 heteroatoms selected from the group consisting of a nitrogen atom, an oxygen atom and a sulfur atom as a ring-constituting atom. When there are two or more heteroatoms, they may be the same or different.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, a tetrazolyl group and the like.

Examples of the 6-membered heteroaryl group include a pyridyl group, a pyrazinyl group, a pyrimidinyl group, a pyridazinyl group, a triazinyl group and the like.

Examples of the substituents on the "C3-6 cycloalkyl group", the "phenyl group", or the "5-6 membered heteroaryl group" for $R^2$ include halogeno groups such as a fluoro group, a chloro group, a bromo group, an iodo group or the like; C1-6 alkyl groups such as a methyl group, an ethyl group, an n-propyl group, an i-propyl group, an n-butyl group, an s-butyl group, an i-butyl group, a t-butyl group, an n-pentyl group, an n-hexyl group or the like; C1-6 haloalkyl groups such as a chloromethyl group, a chloroethyl group, a trifluoromethyl group, a 1,2-dichloro-n-propyl group, a 1-fluoro-n-butyl group or the like; a hydroxyl group; C1-6 alkoxy groups such as a methoxy group, an ethoxy group, an n-propoxy group, an i-propoxy group, an n-butoxy group, an s-butoxy group, an i-butoxy group, a t-butoxy group or the like; C1-6 haloalkoxy groups such as a 2-chloro-n-propoxy group, a 2,3-dichloro a butoxy group, trifluoromethoxy group or the like; and a cyano group.

Compound (2) used in the present invention may be one synthesized by a known method, or may be a commercially available one which is synthesized by another method.

Although the amount of compound (2) to be used is not particularly limited, it is, for example, 1.0 to 5.0 mol, and preferably 1.5 to 2.0 mol, with respect to 1 mol of compound (1).

Examples of the base present in the first reaction include inorganic bases such as a sodium carbonate, a sodium hydrogen carbonate, a potassium carbonate, a potassium hydrogen carbonate, a sodium hydroxide, a potassium hydroxide, a sodium hydride, a potassium hydride or the like; and organic bases such as a triethylamine, a tetramethylethylenediamine, an N,N-diisopropylamine, an N,N-dimethylaniline, an N,N-diethylaniline, a 4-methylmorpholine, a 1-azabicyclo[2.2.2]octane, a 1,4-diazabicyclo[2.2.2]octane (abbreviation: DABCO), a 1,8-diazabicyclo[5.4.0]undec-7-ene, a 1,5-diazabicyclo[4.3.0]non-5-ene, a pyridine, a 4-(dimethylamino)pyridine, a 2,6 -dimethylpyridine or the like.

Examples of the metal alkoxide present in the first reaction include a sodium methoxide, a sodium ethoxide, a potassium t-butoxide and the like.

Although the amount of the metal alkoxide and the base to be used is not particularly limited, it is, for example, 0.1 to 5.0 mol, preferably 0.2 to 1.0 mol, with respect to 1 mol of compound (1).

Due to the coexistence of the metal alkoxide or the inorganic base with compound (1), some or all of compound (1) may change to compound (1') (enolate-formation), but this has no effect on the first reaction.

[Chemical formula 20]

(1')

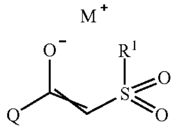

In formula (1'), $M^+$ represents a counter cation, and Q and $R^1$ represent the same as those in formula (1).

The first reaction can be performed without a solvent or in a solvent.

If compound (1) or compound (1') is liquid at the reaction temperature, a solvent may not be used. Considering operability, it is preferable to carry out the first reaction in an organic solvent. The organic solvent is not particularly limited as long as it is inert to compound (1) or compound (1'). Examples of the organic solvent include ethers such as a diethyl ether, a diisopropyl ether, a diethylene glycol dimethyl ether (product name: Diglyme), a tetrahydrofuran (abbreviation: THF) or the like; halogenated hydrocarbons such as a dichloromethane, a chloroform, a 1,2-dichloroethane (abbreviation: DCE) or the like; aliphatic hydrocarbons such as a pentane, a hexane, a cyclohexane, a heptane, an octane or the like; aromatic hydrocarbons such as a toluene, a xylene or the like; aprotic polar solvents such as an N,N-dimethylformamide (abbreviation: DMF), an N,N'-dimethylpropylene urea (abbreviation: DMPU), a hexamethylphosphoric acid triamide (abbreviation: HMPA) or the like; an acetonitrile; and the like. Although the amount of the organic solvent to be used is not particularly limited, it is preferably 5 to 500 parts by weight with respect to 1 part by weight of compound (1) or compound (1').

The order of addition of compound (1), compound (2), a metal alkoxide or a base, and optionally an organic solvent to the first reaction system is not particularly limited.

Compound (3)

Compound (3) is represented by formula (3). Compound (3) can be obtained, for example, by the first reaction.

[Chemical formula 21]

(3)

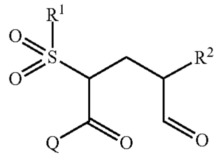

In formula (3), Q, $R^1$ and $R^2$ are the same as those in formula (1) and formula (2).

Compound (3) is preferably a compound represented by formula (3a) (compound (3a)).

[Chemical formula 22]

(3a)

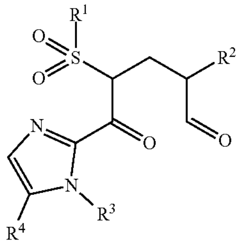

In formula (3a), $R^1$ represents a C1-6 alkyl group, $R^2$ represents a hydrogen atom, a substituted or unsubstituted C1-6 alkyl group, a substituted or unsubstituted C3-6 cycloalkyl group, a substituted or an unsubstituted phenyl group, or a substituted or unsubstituted 5- to 6-membered heteroaryl group, $R^3$ represents a C1-6 alkyl group, and $R^4$ represents a hydrogen atom, a substituted or unsubstituted C1-6 alkyl group, a substituted or unsubstituted C2-6 alkenyl group, or a 1,3-dioxolan-2-yl group.

Compound (3), especially compound (3a), is a useful intermediate in the production of 2-heteroarylpyridine compounds.

<Method for Producing Compound (4)>

Compound (4)

Compound (4) is represented by formula (4).

[Chemical formula 23]

(4)

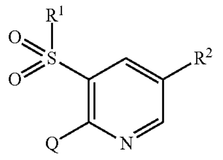

In formula (4), Q, $R^1$ and $R^2$ are the same as those in formula (3).

Compound (4) is preferably a compound represented by formula (4a) (compound (4a)).

[Chemical formula 24]

(4a)

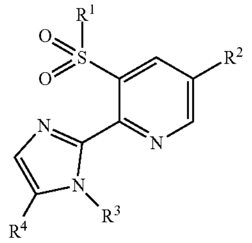

In formula (4a), $R^1$ represents a C1-6 alkyl group, $R^2$ represents a hydrogen atom, a substituted or unsubstituted C1-6 alkyl group, a substituted or unsubstituted C3-6 cycloalkyl group, a substituted or an unsubstituted phenyl group, or a substituted or unsubstituted 5- to 6-membered heteroaryl group, $R^3$ represents a C1-6 alkyl group, and $R^4$ represents a hydrogen atom, a substituted or unsubstituted C1-6 It represents an alkyl group, a substituted or unsubstituted C2-6 alkenyl group, or a 1,3-dioxolan-2-yl group.

Compound (4), especially compound (4a), is the target compound of this production method and is a compound useful as a raw material for agricultural chemicals.

(Second Reaction (A))

One of the methods for producing compound (4) of the present invention including chemically reacting compound (3) with a hydroxylamine or a salt thereof (hereinafter sometimes referred to as the second reaction (A)); and subjecting the product of second reaction (A) to a dehydration reaction.

The hydroxylamine used in the second reaction (A) is an inorganic compound represented by the rational formula $NH_2OH$.

The hydroxylamine salt used in the second reaction (A) is a compound produced by a neutralization reaction between a hydroxylamine and an acid. Specific examples of the hydroxylamine salts include a hydroxylamine sulfate, a hydroxylamine hydrochloride, a hydroxylamine oxalate, a hydroxylamine phosphate and the like.

Although the amount of the hydroxylamine to be used is not particularly limited, it is, for example, 1.0 to 5.0 mol, preferably 1.1 to 2.0 mol, with respect to 1 mol of compound (3).

Although the amount of the hydroxylamine salt to be used is not particularly limited, it is, for example, 1.0 to 5.0 mol, and preferably 1.1 to 2.0 mol with respect to 1 mol of compound (3) if it is a monovalent acid salt, and 0.5 to 2.5 mol, and preferably 0.55 to 1.0 mol with respect to 1 mol of compound (3) if it is a divalent acid salt.

A solvent can be used in the second reaction (A). Examples of the solvents that can be used include water, organic solvents, mixed solvents of water and organic solvents, mixed solvents of organic solvents, and the like.

Examples of the organic solvent include alcohols such as a methanol, an ethanol or the like; ethers such as a diethyl ether, a diisopropyl ether, a diethylene glycol dimethyl ether (product name: Diglyme), a tetrahydrofuran (abbreviation: THF) or the like; esters such as an ethyl acetate or the like; halogenated hydrocarbons such as a dichloromethane, a chloroform, a 1,2-dichloroethane (abbreviation: DCE) or the like; aliphatic hydrocarbons such as a pentane, a hexane, a cyclohexane, a heptane, an octane or the like; aromatic hydrocarbons such as a toluene, a xylene or the like; aprotic polar solvents such as an N,N-dimethylformamide (abbreviation: DMF), an N,N'-dimethylpropylene urea (abbreviation: DMPU), a hexamethylphosphoric acid triamide (abbreviation: HMPA) or the like; an acetonitrile; and the like.

The amount of the solvent to be used is preferably 5 to 500 parts by weight with respect to 1 part by weight of compound (3).

The order of addition of compound (3), a hydroxylamine or a hydroxylamine salt, and optionally a solvent to the second reaction (A) system is not particularly limited.

One embodiment includes obtaining a mixed solution by mixing compound (1) and compound (2) together in an organic solvent or without a solvent, completing the first reaction by adding a metal alkoxide or a base to the mixed solution and stirring, completing the second reaction (A) by adding a hydroxylamine or a hydroxylamine salt to a liquid containing the product of the first reaction (compound (3)) and stirring, followed by subjecting to a dehydration reaction.

Each substance may be added in its entirety at once or in small amounts gradually.

The reaction may be carried out in such a manner that the first reaction, the second reaction (A) and the dehydration reaction are carried out sequentially in a single reactor, or may be carried out in such a manner that the first reaction is carried out in a first reactor, the product of the first reaction is transferred to a second reactor to carry out the second reaction (A) in the second reactor, and the product of the second reaction (A) is transferred to a third reactor to carry out the dehydration reaction in the third reactor.

After the first reaction or the second reaction (A) is completed, extraction is performed with an organic solvent, and the resulting organic layer is subjected to post-treatments such as drying and concentration. Furthermore, if necessary, the product of the first reaction may be purified by recrystallization, chromatography or the like.

The temperature during the first reaction is not particularly limited, and is, for example, 0° C. to 50° C. The pressure during the first reaction is not particularly limited, and is, for example, 0.1 to 1 MPa, and preferably 0.1 to 0.5 MPa. The reaction time is not particularly limited, and is, for example, 0.5 to 24 hours. The first reaction is preferably carried out under an inert gas atmosphere.

The temperature during the second reaction (A) can be selected as appropriate, and is for example, 50° C. to 120° C. To obtain a high temperature, heating may be carried out under reflux. In the heating under reflux, the low-boiling substances generated in the first reaction or the like may be distilled off. Although the pressure during the second reaction (A) is not particularly limited, it is, for example, 0.1 to 1 MPa, and preferably 0.1 to 0.5 MPa. The time for the second reaction (A) is, for example, 1 hour to 24 hours. The second reaction is preferably carried out under an inert gas atmosphere.

Although the details are unknown, it is presumed that the products of the second reaction (A) are represented by formulas (6), (7) or the like.

[Chemical formula 25]

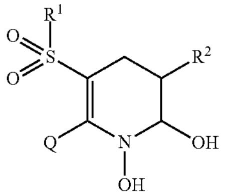

(6)

[Chemical formula 26]

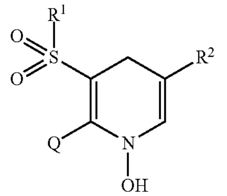

(7)

In formulas (6) and (7), Q, $R^1$ and $R^2$ are the same as those in formula (3).

Compound (4) can be obtained by subjecting the product of the second reaction (A) to a dehydration reaction.

Although the dehydration reaction may proceed simply by applying heat, that is, by heating, it is preferable to use a dehydrating agent to promote the dehydration reaction.

The dehydrating agent is not particularly limited as long as it has the effect of desorbing hydrogen atoms and oxygen atoms in the product of the second reaction (A) as water molecules. Examples of the dehydrating agents include a concentrated sulfuric acid, a diphosphorus pentoxide, an anhydrous zinc chloride, an acetyl chloride, an acetic anhydride, an oxalic acid, a polyphosphoric acid, a magnesium sulfate, a zinc chloride, an alumina, a molecular sieve and the like.

Although the amount of the dehydrating agent to be used is not particularly limited, it is, for example, 1.0 to 5.0 mol, and preferably 1.1 to 2.0 mol, with respect to 1 mol of compound (3).

Although the temperature during the dehydration reaction is not particularly limited, it is, for example, from 60° C. to the boiling point of the solvent used. Although the pressure during the dehydration reaction is not particularly limited, it is, for example, 0.1 to 1 MPa, and preferably 0.1 to 0.5 MPa. Although the reaction time is not particularly limited, it is, for example, 1 hour to 24 hours. The dehydration reaction can be performed under an inert gas atmosphere.

After the completion of the dehydration reaction, post-treatments such as extraction with an organic solvent and drying and concentration of the resulting organic layer are performed. Further, if necessary, purification can be performed by recrystallization, chromatography or the like.

(Second Reaction (B))

Another one of the methods for producing compound (4) of the present invention includes chemically reacting a compound represented by formula (3) with an ammonia or an ammonium salt in the presence of an alcohol (hereinafter sometimes referred to as second reaction (B)), and oxidizing the product of the above chemical reaction in the presence of an organic oxidizing agent.

As the ammonia used in the second reaction (B), in addition to ammonia gas, a methanol solution of ammonia, an ethanol solution of ammonia, an isopropanol solution of ammonia, a 1,4-dioxane solution of ammonia, or a tetrahydrofuran solution of ammonia may also be used.

Specific examples of the ammonium salt used in the second reaction (B) include an ammonium chloride, an ammonium acetate, an ammonium carbamate, an ammonium formate, an ammonium hydrogen carbonate, ammonium carbonate and the like.

Although the amount of the ammonia or the ammonium salt to be used is not particularly limited, it is, for example, 1.0 to 5.0 mol, and preferably 1.1 to 4.0 mol, with respect to 1 mol of compound (3).

An alcohol is used in the second reaction (B). Specific examples include a methanol, an ethanol, an n-propanol, an isopropanol and the like. Although the amount of the alcohol to be used is not particularly limited, it is preferably 5 to 100 parts by weight with respect to 1 part by weight of compound (3).

Other organic solvents may be used in addition to the alcohol. Said other organic solvents are not particularly limited as long as they are inert to compound (3).

An acid may be added to accelerate the reaction. Examples of the acid include carboxylic acids such as an acetic acid, a formic acid, an oxalic acid, a benzoic acid, 4-chlorobenzoic acid or the like; a phosphoric acid; sulfonic acids such as a methanesulfonic acid, a 4-toluenesulfonic acid monohydrate, a trifluoromethanesulfonic acid or the like; hydrogen halides such as a hydrogen chloride, a hydrogen bromide, a hydrogen iodide, hydrogen fluoride or the like; a sulfuric acid, a nitric acid, a tetrafluoroboric acid, and the like, and a carboxylic acid is preferable, and an acetic acid is more preferable.

Although the amount of the acid to be used is not particularly limited, it is usually 0.1 to 10 mol with respect to 1 mol of compound (3).

The order of addition of compound (3), an alcohol, an ammonia or an ammonium salt, and optionally an organic solvent to the second reaction (B) system is not particularly limited.

One embodiment includes obtaining a mixed solution by mixing compound (1) and compound (2) together in an organic solvent or without a solvent, completing the first reaction by adding a metal alkoxide or a base to the mixed solution and stirring, completing the second reaction (B) by adding an alcohol and an ammonia or an ammonium salt to a liquid containing the product of the first reaction (compound (3)) and stirring, followed by oxidizing.

Each substance may be added in its entirety at once or in small amounts gradually.

The reaction may be carried out in such a manner that the first reaction, the second reaction (B) and the oxidizing are carried out sequentially in a single reactor, or may be carried out in such a manner that the first reaction is carried out in a first reactor, the product of the first reaction is transferred to a second reactor to carry out the second reaction (B) in the second reactor, and the product of the second reaction (A) is transferred to a third reactor to carry out the oxidizing in the third reactor.

After the first reaction or the second reaction (B) is completed, extraction is performed with an organic solvent, and the resulting organic layer is subjected to post-treatments such as drying and concentration. Furthermore, if necessary, the product of the first reaction may be purified by recrystallization, chromatography or the like.

The temperature during the first reaction is not particularly limited, and is, for example, 0° C. to 50° C. The pressure during the first reaction is not particularly limited, and is, for example, 0.1 to 1 MPa, and preferably 0.1 to 0.5 MPa. The reaction time is not particularly limited, and is, for example, 0.5 to 24 hours. The first reaction is preferably carried out under an inert gas atmosphere.

The temperature during the second reaction (B) can be selected as appropriate, and is for example, 50° C. to 120° C. The temperature depends on the boiling point of the alcohol to be used. To obtain a high temperature, heating may be carried out under reflux. In the heating under reflux, the low-boiling substances generated in the first reaction or the like may be distilled off. Although the pressure during the second reaction (B) is not particularly limited, it is, for example, 0.1 to 1 MPa, and preferably 0.1 to 0.5 MPa. The time for the second reaction (B) is, for example, 1 hour to 24 hours. The second reaction (B) is preferably carried out under an inert gas atmosphere.

Although the details are unknown, it is presumed that the products of the second reaction (B) are represented by formulas (8), (9) or the like.

[Chemical formula 27]

(8)

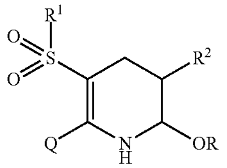

[Chemical formula 28]

(9)

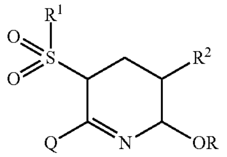

In formulas (8) and (9), Q, $R^1$ and $R^2$ are the same as those in formula (3). R in the formula is an alkyl group derived from the alcohol used. If the alcohol used is a methanol, it is a methyl group, and if the alcohol used is an ethanol, it is an ethyl group.

Compound (4) can be obtained by oxidizing the product of the second reaction (B) in the presence of an organic oxidizing agent.

Examples of the organic oxidizing agent include p-quinone oxidizing agents such as a p-benzoquinone, a chloranil, and 2,3-dichloro-5,6-dicyano-1,4-benzoquinone (DDQ) or the like; o-quinone oxidizing agents such as an o-benzoquinone or the like; N-halosuccinimide oxidizing agents such as an N-chlorosuccinimide, an N-bromosuccinimide or the like; hypervalent iodine oxidizing agents such as a (diacetoxyiodo)benzene, a 2-iodoxybenzoic acid or the like; N-oxide compounds such as a pyridine N-oxide, a 4-chloropyridine N-oxide, a 2,6-lutidine N-oxide or the like; and the like. As the oxidizing agent, a p-quinone oxidizing agent is preferable.

Although the amount of the organic oxidizing agent to be used is not particularly limited, it is, for example, 1.0 to 10.0 mol, and preferably 1.0 to 5.0 mol, with respect to 1 mol of compound (3).

The oxidation reaction is usually carried out in an organic solvent. The organic solvent is not particularly limited as long as it is inert to the product of the second reaction (B). For example, alcohols such as a methanol, an ethanol, an isopropanol or the like; ethers such as a diethyl ether, a diisopropyl ether, a diethylene glycol dimethyl ether (product name: Diglyme), a tetrahydrofuran (abbreviation: THF) or the like; halogenated hydrocarbons such as a dichloromethane, a chloroform, a 1,2-dichloroethane (abbreviation: DCE) or the like; aliphatic hydrocarbons such as a pentane, a hexane, a cyclohexane, a heptane, an octane or the like; aromatic hydrocarbons such as a toluene, a xylene or the like; aprotic polar solvents such as an N,N-dimethylformamide (abbreviation: DMF), an N,N'-dimethylpropylene urea (abbreviation: DMPU), a hexamethylphosphoric acid triamide (abbreviation: HMPA) or the like; an acetonitrile; and the like. Although the amount of the organic solvent to be used is not particularly limited, it is preferably 10 to 500 parts by weight with respect to 1 part by weight of compound (3).

An acid may be added to accelerate the reaction. Examples of the acid include carboxylic acids such as an acetic acid, a formic acid, an oxalic acid, a benzoic acid, 4-chlorobenzoic acid or the like; a phosphoric acid; sulfonic acids such as a methanesulfonic acid, a 4-toluenesulfonic acid monohydrate, a trifluoromethanesulfonic acid or the like; hydrogen halides such as a hydrogen chloride, a hydrogen bromide, a hydrogen iodide, hydrogen fluoride or the like; a sulfuric acid, a nitric acid, a tetrafluoroboric acid, and the like, and a carboxylic acid is preferable, and an acetic acid is more preferable.

Although the amount of the acid to be used is not particularly limited, it is usually 0.01 to 100 mol with respect to 1 mol of compound (3).

Although the temperature at which the oxidation reaction is carried out is not particularly limited, it is, for example, between −20° C. and 120° C., or between −20° C. and the boiling point of the solvent to be used. Although the pressure when carrying out the oxidation reaction is not particularly limited, it is, for example, 0.1 to 1 MPa, and preferably 0.1 to 0.5 MPa. Although the reaction time is not particularly limited, it is, for example, 0.5 to 24 hours. The oxidation reaction can be carried out under an inert gas atmosphere.

After the oxidation reaction is completed, post-treatments such as extraction with an organic solvent and drying and concentration of the resulting organic layer are performed. Further, if necessary, purification can be performed by recrystallization, chromatography or the like.

The present invention will be described in more detail with reference to the Examples below. Note that the present invention is not limited to the following Examples.

Example 1

2-(5-(2-chloro-3,3,3-trifluoroprop-1-en-1-yl)-1-methyl-1H-imidazol-2-yl)-5-cyclopropyl-3-(ethylsulfonyl)pyridine] was obtained using the following procedure.

Step 1

Preparation of 5-[5-(2-chloro-3,3,3-trifluoroprop-1-en-1-yl)-1-methyl-1H-imidazol-2-yl]-2-cyclopropyl-4-(ethylsulfonyl)-5-oxopentanal]

[Chemical formula 29]

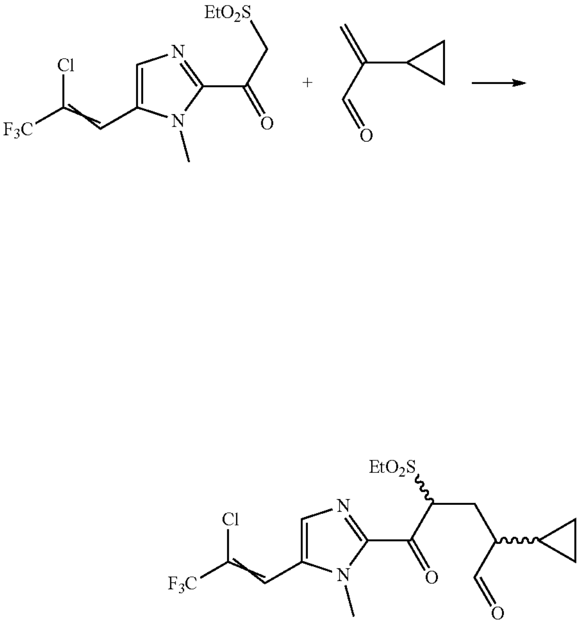

1-[5-(2-chloro-3,3,3-trifluoroprop-1-en-1-yl)-1-methyl-1H-imidazol-2-yl]-2-(ethylsulfonyl) ethan-1-one] (0.697 g, purity: 93.0%, 1.88 mmol) and 2-cyclopropylacrylaldehyde (0.884 g, purity: 40.3%, 3.71 mmol) were dissolved in a mixture of toluene (3.8 mL) and methanol (3.8 mL). The resulting solution was cooled in an ice water bath. Thereafter, sodium methoxide (74.8 μL, 28% methanol solution, 0.38 mmol) was added, and the resulting mixture was stirred for 3.4 hours while cooling in an ice water bath. Thereafter, the temperature was raised to room temperature and stirred for 3.0 hours.

To this was added a half-saturated aqueous solution of ammonium chloride (10 mL), and the organic phase was separated. The aqueous phase was extracted with toluene (10 mL) and the organic phase was separated. The separated organic phases were combined and washed with saturated brine (10 mL). The aqueous phase was separated. The remaining organic phase was dried over sodium sulfate and filtered. The filtrate was concentrated and purified by silica gel column chromatography (developing solvent: hexane/ethyl acetate). The obtained fraction was concentrated to obtain 0.641 g of the target compound (purity: 89.3%, 1.30 mmol, yield: 69%).

Step 2

Preparation of 2-(5-(2-chloro-3,3,3-trifluoroprop-1-en-1-yl)-1-methyl-1H-imidazol-2-yl)-5-cyclopropyl-3-(ethylsulfonyl)pyridine

[Chemical formula 30]

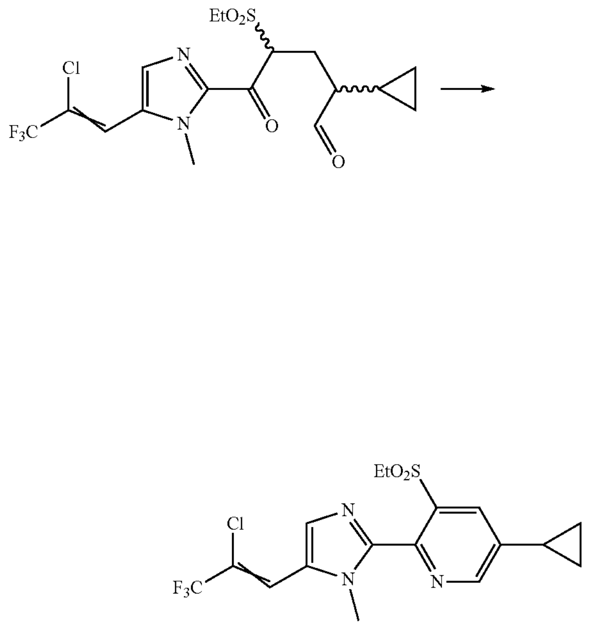

5-[5-(2-chloro-3,3,3-trifluoroprop-1-en-1-yl)-1-methyl-1H-imidazol-2-yl]-2-cyclopropyl-4-(ethylsulfonyl)-5-oxo-pentanal (0.641 g, purity: 89.3%, 1.30 mmol) was dissolved in a mixture of acetonitrile (5.2 mL) and water (1.3 mL). Hydroxylamine sulfate (0.116 g, 0.71 mmol) was added to the resulting solution, heated in a 100° C. oil bath, and refluxed for 4.0 hours.

Next, sulfuric acid (36.6 μL, 0.69 mmol) was added and the resulting mixture was refluxed for 3.0 hours, and further sulfuric acid (36.6 μL, 0.69 mmol) was added and the resulting mixture was refluxed for 2.5 hours.

The resulting liquid was cooled to room temperature. Thereafter, water (10 mL) and 28% aqueous sodium hydroxide solution (600 μL) were added, and the organic phase was separated. The aqueous phase was extracted twice with chloroform (10 mL) and the organic phase was separated. The separated organic phases were combined and washed with water (10 mL) and saturated brine (10 mL). Thereafter, the organic phase was concentrated and purified by silica gel column chromatography (developing solvent: chloroform/ethyl acetate). The obtained fraction was concentrated to obtain 0.121 g of the target compound (purity: 100%, 0.29 mmol, yield: 22%).

Example 2

2-(5-(1,3-dioxolan-2-yl)-1-methyl-1H-imidazol-2-yl)-5-cyclopropyl-3-(ethylsulfonyl)pyridine was obtained using the following procedure.

Step 1

Preparation of 5-[5-(1,3-dioxolan-2-yl)-1-methyl-1H-imidazol-2-yl]-2-cyclopropyl-4-(ethylsulfonyl)-5-oxopentanal

[Chemical formula 31]

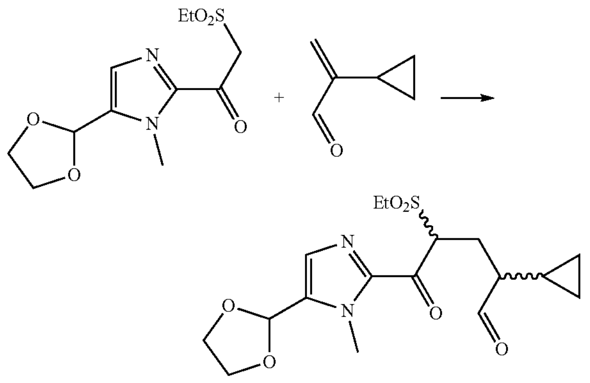

1-[5-(1,3-dioxolan-2-yl)-1-methyl-1H-imidazol-2-yl]-2-(ethylsulfonyl) ethan-1-one (1.445 g, purity: 100%, 5.01 mmol) and 2-cyclopropylacrylaldehyde (2.485 g, purity: 38.5%, 9.95 mmol) were dissolved in a mixture of toluene (10 mL) and methanol (10 mL). Sodium methoxide (200 μL, 28% methanol solution, 1.00 mmol) was added to this, and the resulting mixture was stirred at room temperature for 3.9 hours.

To this, a half-saturated aqueous ammonium chloride solution (25 mL) was added, and the organic phase was separated. The aqueous phase was extracted twice with chloroform (25 mL) and the organic phase was separated. The separated organic phases were combined, washed with saturated brine (25 mL), and the aqueous phase was separated. The organic phase that remained was dried over sodium sulfate and filtered. The filtrate was concentrated and purified by silica gel column chromatography (developing solvent: chloroform/acetonitrile). The obtained fraction was concentrated to obtain 1.783 g of the target compound (purity: 100%, 4.63 mmol, yield: 93%).

Step 2

Preparation of 2-(5-(1,3-dioxolan-2-yl)-1-methyl-1H-imidazol-2-yl)-5-cyclopropyl-3-(ethylsulfonyl) pyridine

[Chemical formula 32]

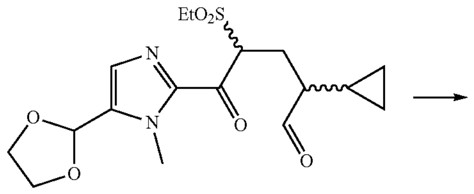

-continued

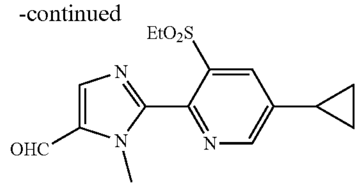

An aqueous hydroxylamine solution (88.4 μL, purity: 50%, 1.50 mmol) was added to an acetonitrile solution of 5-[5-(1,3-dioxolan-2-yl)-1-methyl-1H-imidazol-2-yl]-2-cyclopropyl-4-(ethylsulfonyl)-5-oxopentanal (6.267 g, purity: 9.2%, 1.50 mmol), and the resulting mixture was stirred at room temperature for 2.5 hours.

To this, sulfuric acid (42.2 μL, 0.75 mmol) was added, and the resulting mixture was refluxed for 4.3 hours, and water (300 μL) and sulfuric acid (42.2 μL, 0.75 mmol) were further added, and the resulting mixture was refluxed for 3.2 hours.

The obtained liquid was cooled to room temperature. Then, saturated sodium bicarbonate solution (10 mL) was added, and the resulting mixture was extracted twice with dichloromethane (10 mL). The organic phases were combined, dried over sodium sulfate and filtered. The filtrate was concentrated and purified by silica gel column chromatography (developing solvent: chloroform/acetonitrile). The obtained fraction was concentrated to obtain 0.078 g of the target compound (purity: 100%, 0.24 mmol, yield: 16%).

Example 3

2-(5-(2-chloro-3,3,3-trifluoroprop-1-en-1-yl)-1-methyl-1H-imidazol-2-yl)-5-cyclopropyl-3-(ethylsulfonyl)pyridine] was obtained using the following procedure.

[Chemical formula 33]

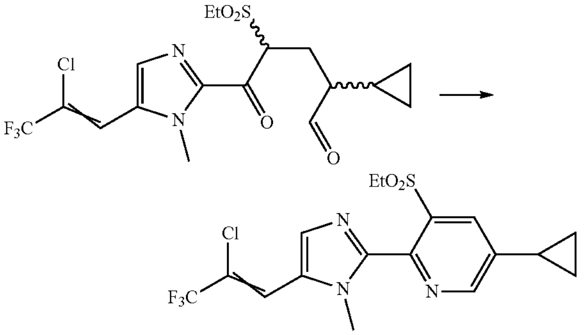

Methanol (2 mL) and acetic acid (0.12 g, 4.00 mmol) were added to a methanol solution of 5-[5-(2-chloro-3,3,3-trifluoroprop-1-en-1-yl)-1-methyl-1H-imidazol-2-yl]-2-cyclopropyl-4-(ethylsulfonyl)-5-oxopentanal (2.393 g, purity 36.85%, 2.00 mmol), and the resulting mixture was refluxed. An ammonium acetate aqueous solution (0.37 g, purity: 50%, 2.40 mmol)) was added dropwise thereto, and the resulting mixture was refluxed for 1 hour.

Then, benzoquinone (0.22 g, 2.00 mmol) was added and stirred at room temperature for 2 hours.

Thereafter, acetonitrile (10 mL) was added and dissolved, to obtain 11.91 g of a solution containing the target compound (purity: 4.99%, 1.42 mmol, yield: 70.8%).

INDUSTRIAL APPLICABILITY

The production method of the present invention can efficiently obtain a 2-heteroarylpyridine compound having a sulfur-containing functional group, which is a major partial structure constituting compounds that serve as active ingredients for pharmaceuticals and agricultural chemicals.

The invention claimed is:

1. A method for producing a compound represented by formula (3), comprising:

chemically reacting a compound represented by formula (1) with a compound represented by formula (2) in the presence of a metal alkoxide or a base, (1)

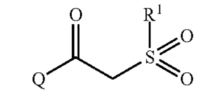

in formula (1), Q represents a substituted or unsubstituted 5- to 6-membered or 9- to 10-membered heteroaryl group, and $R^1$ represents a C1-6 alkyl group, (2)

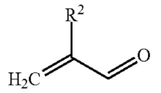

in formula (2), $R^2$ represents a hydrogen atom, a substituted or unsubstituted C1-6 alkyl group, a substituted or unsubstituted C3-6 cycloalkyl group, a substituted or unsubstituted phenyl group, or a substituted or unsubstituted 5- to 6-membered heteroaryl group, (3)

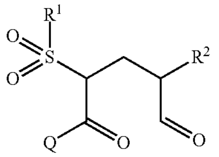

in formula (3), Q, $R^1$ and $R^2$ are the same as those in formula (1) and formula (2).

2. The method according to claim 1, wherein Q in formula (1) and formula (3) is a group represented by formula (5), (5)

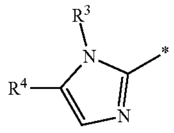

in formula (5), * represents a bonding site, $R^3$ represents a C1-6 alkyl group, $R^4$ represents a hydrogen atom, a substituted or unsubstituted C1-6 alkyl group, a substituted or unsubstituted C2-6 alkenyl group, or a 1,3-dioxolan-2-yl group.

* * * * *